US011097115B2

(12) United States Patent
Cong

(10) Patent No.: US 11,097,115 B2
(45) Date of Patent: Aug. 24, 2021

(54) IMPLANTABLE PULSE GENERATOR WITH SUTURE HOLES AND METHODS FOR IMPLANTING THE SAME

(71) Applicant: Galvani Bioelectronics Limited, Middlesex (GB)

(72) Inventor: Peng Cong, Burlingame, CA (US)

(73) Assignee: Galvani Bioelectronics Limited, Middlesex (GB)

(*) Notice: Subject to any disclaimer, the term of this patent is extended or adjusted under 35 U.S.C. 154(b) by 0 days.

(21) Appl. No.: 16/140,471

(22) Filed: Sep. 24, 2018

(65) Prior Publication Data

US 2020/0094064 A1    Mar. 26, 2020

(51) Int. Cl.
*A61N 1/00* (2006.01)
*A61N 1/375* (2006.01)
(Continued)

(52) U.S. Cl.
CPC ...... *A61N 1/37518* (2017.08); *A61B 17/0469* (2013.01); *A61B 17/3468* (2013.01);
(Continued)

(58) Field of Classification Search
CPC ............ A61N 1/37518; A61N 1/37229; A61N 1/376; A61N 1/3605; A61B 17/0469; A61B 17/3468
(Continued)

(56) References Cited

U.S. PATENT DOCUMENTS

| 4,441,498 A |   | 4/1984 | Nordling |
| 5,948,001 A | * | 9/1999 | Larsen ............... A61B 17/0469 606/104 |

(Continued)

FOREIGN PATENT DOCUMENTS

| WO | 2006126201    | 11/2006 |
| WO | WO-2006126201 A2 * | 11/2006 ............. A61N 1/375 |

OTHER PUBLICATIONS

International Application No. PCT/US2019/052403, "International Search Report and Written Opinion", dated Nov. 19, 2019, 16 pages.

*Primary Examiner* — Carl H Layno
*Assistant Examiner* — Michael J Lau
(74) *Attorney, Agent, or Firm* — Brett A. Lovejoy; Morgan, Lewis & Bockius, LLP

(57) ABSTRACT

An implantable pulse generator is provided that includes a power source, a wireless communication component configured to facilitate wireless communication with a non-implanted device and pulse-generating circuitry connected to the power source. The pulse-generating circuitry can be configured to identify, based on wireless communication with the non-implanted device, temporal and amplitude characteristics for electrical pulse stimuli and to trigger electrical output stimuli having the temporal and amplitude characteristics. The implantable pulse generation can further include one or more lead connections—each being shaped to engage a lead and electrically connected to the pulse-generating circuitry to enable the lead to deliver at least part of the electrical output stimuli triggered by the pulse-generating circuitry. The implantable pulse generator can further include one or more suture-engagement components, each including one or more holes each having a diameter that is at least 0.1 mm and less than 5 mm.

16 Claims, 7 Drawing Sheets

(51) Int. Cl.
*A61B 17/34* (2006.01)
*A61N 1/372* (2006.01)
*A61B 17/04* (2006.01)
*A61N 1/378* (2006.01)
*A61N 1/36* (2006.01)

(52) U.S. Cl.
CPC ......... *A61N 1/378* (2013.01); *A61N 1/37229* (2013.01); *A61N 1/3605* (2013.01)

(58) Field of Classification Search
USPC ........................... 607/149, 37; 600/116–117
See application file for complete search history.

(56) References Cited

U.S. PATENT DOCUMENTS

| | | | | |
|---|---|---|---|---|
| 5,987,352 | A * | 11/1999 | Klein | A61N 1/375 600/509 |
| 6,496,715 | B1 * | 12/2002 | Lee | A61N 1/372 600/424 |
| 6,505,073 | B2 * | 1/2003 | Gramse | A61N 1/375 607/37 |
| 7,563,141 | B2 * | 7/2009 | Alexander | A61N 1/0529 439/669 |
| 7,758,384 | B2 * | 7/2010 | Alexander | H01R 31/06 439/623 |
| 8,929,986 | B2 | 1/2015 | Parker et al. | |
| 9,511,227 | B2 | 12/2016 | Biele et al. | |
| 9,886,002 | B2 | 2/2018 | Morioka et al. | |
| 2003/0105469 | A1 * | 6/2003 | Karmon | A61B 17/7097 606/92 |
| 2004/0199166 | A1 * | 10/2004 | Schmieding | A61B 17/1617 606/79 |
| 2005/0283170 | A1 * | 12/2005 | Battles | A61B 17/0482 606/144 |
| 2006/0237023 | A1 * | 10/2006 | Cox | A61B 17/0401 128/898 |
| 2008/0015540 | A1 * | 1/2008 | Muni | A61B 17/3421 604/500 |
| 2008/0076959 | A1 * | 3/2008 | Farnan | A61M 1/122 600/16 |
| 2008/0097487 | A1 * | 4/2008 | Pool | A61F 5/0053 606/151 |
| 2008/0097496 | A1 * | 4/2008 | Chang | A61B 17/064 606/157 |
| 2008/0103407 | A1 * | 5/2008 | Bolea | A61N 1/3601 600/529 |
| 2008/0103577 | A1 * | 5/2008 | Gerber | H04N 21/435 607/149 |
| 2008/0243144 | A1 * | 10/2008 | Laufer | A61B 17/0401 606/139 |
| 2009/0171142 | A1 * | 7/2009 | Chu | A61B 17/0401 600/37 |
| 2009/0182188 | A1 * | 7/2009 | Marseille | A61M 1/3653 600/16 |
| 2010/0025527 | A1 * | 2/2010 | Lal | A61N 1/3605 244/1 R |
| 2011/0319932 | A1 * | 12/2011 | Avelar | A61B 17/06166 606/228 |
| 2012/0059467 | A1 | 3/2012 | Drew et al. | |
| 2012/0283754 | A1 * | 11/2012 | Murillo | A61B 17/0469 606/145 |
| 2013/0085513 | A1 * | 4/2013 | North | A61M 25/02 606/148 |
| 2013/0238023 | A1 * | 9/2013 | Wales | A61B 17/0401 606/232 |
| 2014/0018885 | A1 * | 1/2014 | Pianca | A61N 1/0551 607/72 |
| 2014/0228905 | A1 * | 8/2014 | Bolea | A61F 5/56 607/42 |
| 2014/0243593 | A1 * | 8/2014 | Goode | A61B 18/082 600/104 |
| 2014/0243624 | A1 * | 8/2014 | Farra | A61M 5/14276 600/302 |
| 2015/0150699 | A1 * | 6/2015 | Pattison | A61F 5/0036 606/192 |
| 2015/0257755 | A1 * | 9/2015 | North | A61B 17/0485 604/506 |
| 2015/0272585 | A1 * | 10/2015 | Park | A61B 17/1227 606/157 |
| 2015/0290465 | A1 * | 10/2015 | Mashiach | H02J 50/12 607/61 |
| 2016/0015988 | A1 * | 1/2016 | Perryman | A61N 1/36071 606/129 |
| 2016/0023012 | A1 * | 1/2016 | Ries | A61N 1/37518 607/116 |
| 2016/0242761 | A1 * | 8/2016 | Lore | A61B 17/0401 |
| 2016/0262780 | A1 * | 9/2016 | Kucklick | A61B 17/3462 |
| 2016/0331978 | A1 | 11/2016 | Tischendorf et al. | |
| 2017/0202467 | A1 * | 7/2017 | Zitnik | A61N 1/36053 |
| 2017/0273733 | A1 * | 9/2017 | Weber | A61B 18/1402 |
| 2017/0281957 | A1 * | 10/2017 | Howard | A61N 1/3754 |
| 2018/0071522 | A1 | 3/2018 | Feldman et al. | |
| 2018/0085593 | A1 * | 3/2018 | Fayram | H02J 50/80 |
| 2018/0154156 | A1 * | 6/2018 | Clark | A61N 1/36053 |
| 2018/0185661 | A1 * | 7/2018 | Imran | A61M 31/002 |
| 2018/0264270 | A1 * | 9/2018 | Koop | A61N 1/36507 |
| 2019/0388696 | A1 * | 12/2019 | Armesto | A61N 1/057 |

\* cited by examiner

IMPLANTABLE PULSE GENERATOR WITH SUTURE HOLES AND METHODS FOR IMPLANTING THE SAME

FIELD

Embodiments relate to an implantable stimulating device. Specifically, some embodiments relate to an implantable pulse generator device that includes one or more suture holes and/or an antenna with a 2-D form factor.

BACKGROUND

Many biological processes are mediated by intrinsic electrical activity. Occasionally, diseases or medical conditions affect these biological processes and thereby result in irregular or altered electrical activity. Impaired electrical activity can result in cardiac deficits, impaired sensation, deteriorated motor function and even death. Various medical devices have been designed to modify and/or partly control electrical activity, so as to reduce the probability or magnitude of potential symptoms. For example, pacemakers have been used to control the electrical signals of the heart. It would be desirable to develop other medical devices that can precisely stimulate individual nerves and that can placed securely without causing substantial damage to adjacent tissue.

SUMMARY

In some embodiments, an implantable pulse generator is provided that includes a power source, a wireless communication component configured to facilitate wireless communication with a non-implanted device and pulse-generating circuitry connected to the power source. The pulse-generating circuitry can be configured to identify, based on wireless communication with the non-implanted device, temporal and amplitude characteristics for electrical pulse stimuli and to trigger electrical output stimuli having the temporal and amplitude characteristics. The implantable pulse generation can further include one or more lead connections—each being shaped to engage a lead and electrically connected to the pulse-generating circuitry to enable the lead to deliver at least part of the electrical output stimuli triggered by the pulse-generating circuitry. The implantable pulse generator can further include one or more suture-engagement components, each including one or more holes each having a diameter that is at least 0.1 mm and less than 5 mm.

In some instances, a method for implanting an implantable pulse generator is provided. A trocar can be inserted into a person such that an obturator is near a target anatomical location (e.g., an abdominal muscle). The trocar can include the obturator and a cannula that extends from an opening in the trocar to the obturator. An implantable pulse generator can be inserted into the opening in the trocar to facilitate advancement of the implantable pulse generator through the cannula of the trocar. The implantable pulse generator can include pulse-generating circuitry configured to identify temporal and amplitude characteristics for electrical pulse stimuli and trigger electrical output stimuli having the temporal and amplitude characteristics. The implantable pulse generator can further include one or more lead connections—each shaped to engage a lead and electrically connected to the pulse-generating circuitry to enable the lead to deliver at least part of the electrical output stimuli triggered by the pulse-generating circuitry. The implantable pulse generator can further include one or more suture-engagement components—each including one or more holes. The method can further include positioning a suture grasper device such that a set of grasping jaws of the suture grasper device extend through the cannula of the trocar, tips of the set of grasping jaws are near the target anatomical location, and one or more handle controls remain outside of the opening. The suture grasper device can be configured such that one or more positions of the one or more handle controls control whether the tips of the set of grasping jaws are open or closed. The method can further include controlling the one or more positions of the one or more handle controls across a period of time so as to cause the tips of the set of grasping jaws to facilitate threading a suture through a hole of the one or more holes and an anatomical site at the target anatomical location and to further cause knotting the suture, to thereby at least partly affixed the implantable pulse generator to the target anatomical location.

In some embodiments, a method of manufacturing an implantable pulse generator is provided. The method can include electrically connecting each of one or more lead connections with pulse-generating circuitry, where the pulse-generating circuitry is configured to identify temporal and amplitude characteristics for electrical pulse stimuli and trigger electrical output stimuli having the temporal and amplitude characteristics. The method can also include forming or securing one or more external surfaces such that the pulse-generating circuitry is within the one or more external surfaces, wherein the one or more external surfaces includes or is further processed to include: one or more holes each having a diameter that is at least 0.1 mm and less than 5 mm.

BRIEF DESCRIPTION OF THE DRAWINGS

Illustrative embodiments of the present invention are described in detail below with reference to the following drawing figures.

DESCRIPTION

Figure 1A:
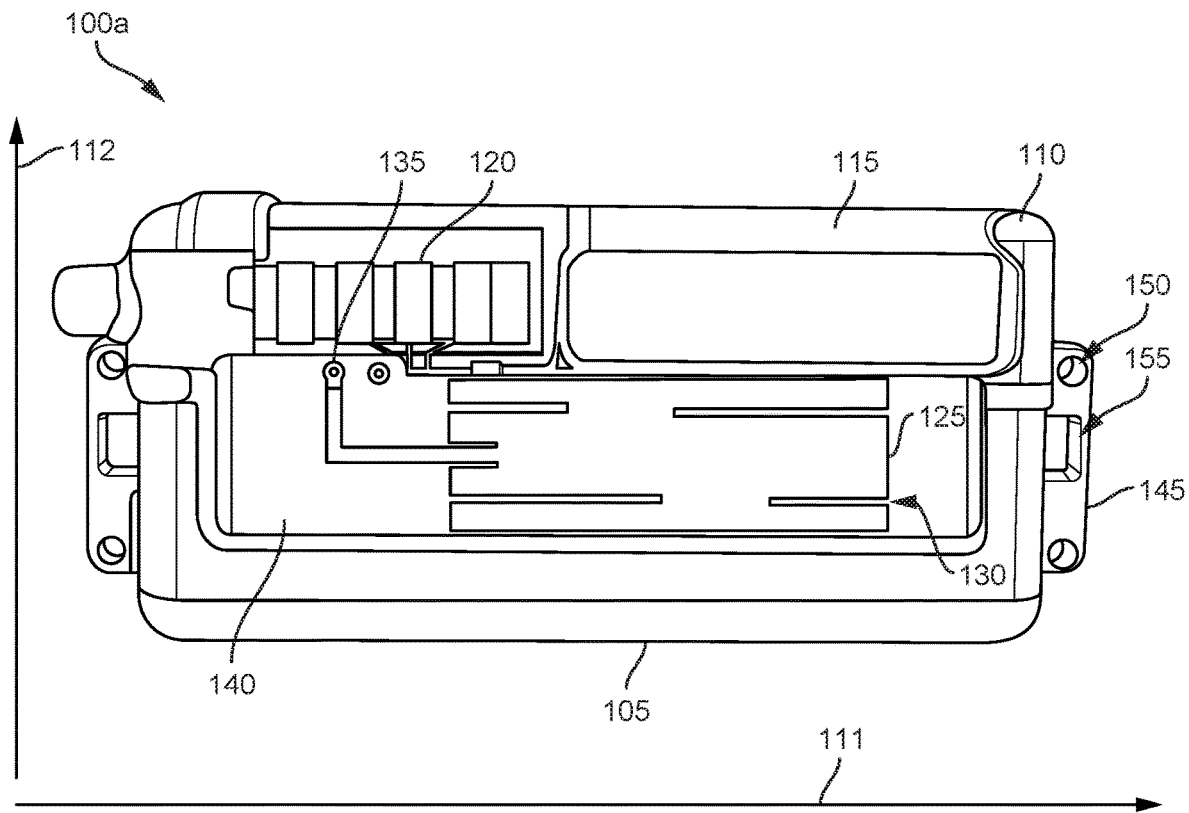
FIG. 1A-1B show multiple views of an implantable pulse generator according to an embodiment of the invention.

Implantable devices have the potentially to directly affect very specific parts of the body. However, both implantation process and the maintained internal positioning of the implantable device is associated with substantial risks. For example, during the implantation process, surrounding tissue may be damaged. As another example, after the device is implanted, the surrounding area may become inflamed. As yet another example, after the device is implanted, it may move from a target location, which may cause further tissue damage and/or inflammatory responses. Thus, it would be desirable to configure a device and implantation process to reduce the risk of tissue damage, inflammatory response and device movement.

In some embodiments, components and spatial features of the implantable device can facilitate reducing these risks. For example, incorporating suture-engagement components in the device (e.g., one or more tabs, hooks, holes, channels, etc.) can facilitate implanting the device through a smaller pathway (and/or while contacting fewer anatomical structures) and/or can facilitate stably securing the device at a target location. A suture-engagement component can include or can have a planar shape, a flat surface, a rounded surface (e.g., at an edge) and/or a wrapped surface (e.g., a c-shaped surface, which may wrap around one or more internal parts of the implantable device). A suture-engagement component can be rigid and can include (for example) a metallic material, a metal, titanium and/or a polymer. In some instances, a suture-engagement component includes a same material as included in a housing of the implantable device. In some instances, a composition of a suture-engagement component is the same as a housing of the implantable device. In some instances, a suture-engagement component is an extension of or is part of a housing of the implantable device.

A suture-engagement component may be located such that at least part of the suture-engagement component is part of an outer surface of the implantable device. For example, the suture-engagement component may include a tab, protrusion, edge, hook, J-shaped or L-shaped edge, etc. of the device. The suture-engagement component may have a thickness that is different than (e.g., smaller than or larger than) a median, mean, maximum or center thickness of the device. In some instances, the suture-engagement component may have a thickness that varies across a dimension of the device (e.g., to form a ridge or edge around the device or to taper the thickness across the suture-engagement component). The differential thickness (e.g., within the suture-engagement component and/or relative to another part of the device) can facilitate implanting the device, as it can facilitate grasping the structure, hooking the structure, and so on with a surgical tool. As one particular example, a configuration that includes a protruding thin surface can facilitate implanting the device by gripping (using a surgical tool) the thin surface and pulling or pushing the device to a target location, rather than gripping a wider portion of the device (e.g., which may involve opening the gripping tool wider, which can cause increased damage).

A device may include a single suture-engagement component or a set of suture-engagement components (e.g., two or four suture-engagement components). When a device includes multiple suture-engagement components, the suture-engagement components may be positioned in same, similar or complementary configurations. For example, in instances in which each suture-engagement component includes one or more layers, the suture-engagement components may be configured such that the one or more layers of one suture-engagement component are parallel to (and/or in a same plane as) the one or more layers of each other suture-engagement component.

The suture-engagement component can include one or more holes. The hole(s) can be sized to be large enough to receive a suture. For example, each hole can have a diameter that is at least 0.1, 0.5, 1 or 2 mm. The diameter may be less than (for example) 10 mm, 5 mm, 3 mm or 2 mm (e.g., to facilitate compact design). Upon positioning an implantable location near a target location, the hole(s) can be used to secure the device to the target location. For example, with respect to each of the one or more holes (or a subset thereof) a suture may be threaded through the hole and also threaded through an anatomical structure (e.g., a tissue).

Each hole of the one or more holes may extend through the device along a thickness dimension. Thus, for example, if the suture-engagement component is a single layer, the hole may extend through the layer; if the suture-engagement component includes multiple layers, the hole may extend through each of the multiple layers. Thus, in some instances, the hole includes a channel (e.g., through one or more layers). The suture-engagement components may be positioned or defined such that the implantable device includes holes at opposite sides of the device. For example, one or more holes can be positioned near a first edge of the device (e.g., such that a center of each of the one or more holes is within 20, 10, 5 or 3 mm from the first edge), and one or more other holes can be positioned near a second opposite edge of the device (such that a center of each of the one or more other holes is within 20, 10, 5 or 3 mm from the second opposite edge). In some instances, the implantable device includes at least four holes. In some instances, at least two holes are separated along a length-wise dimension by at least 80%, at least 90% or at least 95% of a length of the device. In some instances, at least two holes are separated along a width-wise dimension by at least 80%, at least 90% or at least 95% of a width of the device.

The implantable device can include an implantable pulse generator. The implantable pulse generator can include pulse-generating circuitry that controls pulses output in connection with the device. For example, the pulse-generating circuitry can be configured to identify temporal and/or amplitude characteristics for pulse stimuli that are to be output by one or more leads that are to be connected to the implantable device. In some instances, the pulse-generating circuitry generates triggers of pulses and/or a time-series stimulation electrical output (e.g., to be delivered to one or more leads). The implantable device can include one or more lead connections (e.g., one or more ports)—each of which can be configured (e.g., shaped and positioned) to physically engage or attach to a lead and electrically connect the lead to the pulse-generating circuitry. The implantable device can further include a power source (e.g., a rechargeable or non-rechargeable battery). The implantable device can also include a wireless communication component to facilitate communication (e.g., via a Bluetooth channel) between the implantable device and another device. The other device can include a non-implanted and/or remote device. The wireless communication component can include an antenna.

As another example of an implantable-device feature that can reduce implantation risks, efficient configuration of the wireless communication component can reduce a size of an implant, so as to reduce the extent to which an implantation process and/or the implantable device's final position affects various anatomical features. For example, the wireless communication component can include an antenna that includes a planar component that is positioned on an external surface of the implantable device. The antenna may be (for example) placed on the can housing. The planar component can include (for example) a conductive material that is of a shape that enables the antenna to transmit and/or receive signals at a target frequency or target frequency range. The shape can include (for example) a square, rectangular, circular or oval shape that can be patterned to (for example) include a set of slots and/or openings at which the conductive material is absent. The antenna can include a 2-D form factor. The slots and/or openings may have an edge or portion of a perimeter that is at a perimeter of the shape. The planar component can be connected (e.g., via a wire) to circuitry (e.g., pulse-generating circuitry) within the implantable device. The connection can (for example) enable the other device to send commands that specify or constrain pulse characteristics of pulses generated by the pulse-generating circuitry.

In some instances, the wireless communication component includes multiple planar components that are separated by an insulating layer (e.g., and connected via a wire). One of the planar components (e.g., a non-external component) can serve as a ground. Thus, the wireless communication component can include a stack, which may be positioned on a housing of the implantable device. The implantable device can (in some instances) include a can housing that houses (for example) pulse-generating circuitry and a power source (e.g., a rechargeable battery) and a header housing (e.g., a header coating) that houses (for example) one or more lead connections and a coil (e.g., for recharging the battery). The coil can include (for example) a conductive wire, such as a gold wire that has multiple turns. For example, the coil may include at least 3, at least 5 or at least 8 turns and/or less than 20, less than 15, or less than 10 turns. A diameter of the turns may be (for example) at least 10 mm, at least 20 mm or at least 50 mm and/or less than 200 mm, less than 100 mm or less than 75 mm. Additional configuration details for potential IPG coils are disclosed in U.S. Application No. 62/730,104, filed on Sep. 12, 2018, which is hereby incorporated by reference in its entirety for all purposes. The wireless communication component can be positioned at least partly on or fully on the can housing and/or at least partly on or fully on the header housing.

Figure 1B:
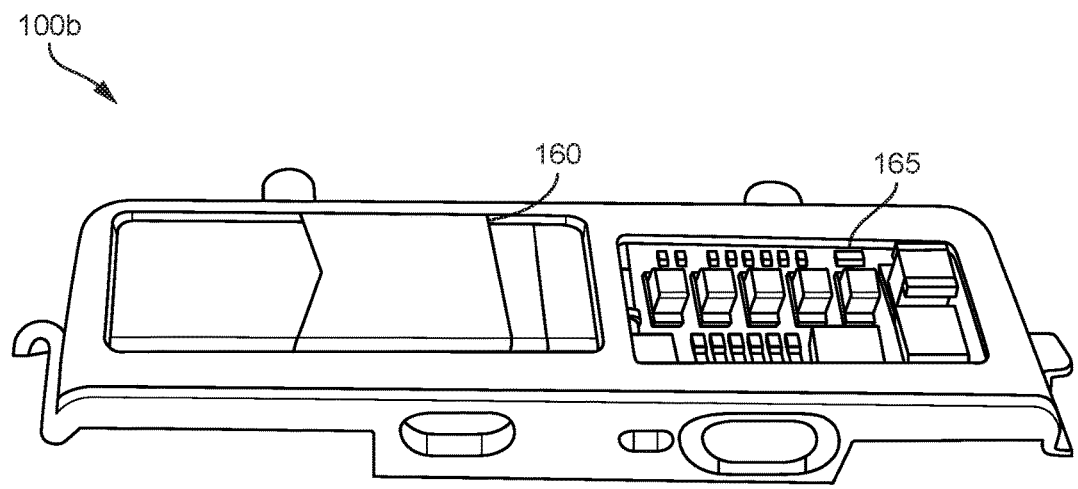

FIG. 1A-1B show multiple views of an implantable pulse generator according to an embodiment of the invention. FIG. 1A shows a front side 100a of the implantable pulse generator. The implantable pulse generator includes a can 105 and a header 110. The implantable device can be characterized as having a length along a length dimension 111, a width along a width dimension 112 and a depth along a depth dimension (perpendicular to each of length dimension 111 and width dimension 112). The length of the device may be (for example) less than 3 inches, less the 2 inches or less than 1 inch. The width of the device may be (for example) less than 2 inches, less than 1 inch or less than 0.5 inch. Can 105 and header 110 can correspond to different portions of the width of the device.

Can 105 includes a housing that houses various components, but also can collectively refer to the can housing and the components housed within the can housing. The can housing can include a metal, such as titanium. The can housing can house (for example) circuitry (e.g., pulse-generating circuitry) and a rechargeable battery. The can housing (e.g., and the implantable device itself) can be hermetically sealed.

Header 110 can include a header housing (e.g., a coating) that houses various components, but also can collectively refer to the header housing and components housed within the header housing. The header housing can include an epoxy or polymer. The header housing can house (for example) a charging coil 115 that is connected to the rechargeable battery and one or more lead connections (e.g., a connector stack 120). Each component (or portion of a component) of the implantable pulse generator that is part of an external surface of the implantable device (e.g., the can housing, the header housing) can be biocompatible.

The implantable device can further include a wireless communication component, such as an antenna 125. The antenna 125 can include (for example) a BLE antenna. The antenna can include a solid conductive material, in which a set of slots 130 protrude. The quantity, locations, widths and lengths of the slots in the set can influence to which frequency antenna 125 is tuned. Antenna configurations are further described in U.S. application Ser. No. 15/969,976, filed on May 3, 2018, which is hereby incorporated by reference in its entirety for all purposes. In some instances, the antenna is configured to have an elliptical polarization, such that emitted fields have elliptical polarization.

The conductive material can extend to connect to one or more vias 135 (or feedthroughs). A via 135 can connect antenna 125 to circuitry, such as pulse-generating circuitry, such that a received signal can influence pulse characteristics. A via 135 can further connect antenna 125 to a ground. In some instances, a can housing can serve as a ground. The wireless communication component may then include (for example) a first conductive layer that is in contact with (e.g., on and/or bonded to) the can housing, a second conductive layer that is part of an external surface of the implantable device, an insulating and low-loss layer 140 (e.g., a ceramic layer or dielectric layer) that is between the first and second conductive layer, a first via that connects the second conductive layer to circuitry inside the can housing, and a second via that connects the second conductive layer to the first conductive layer.

The implantable device can also include one or more suture-engagement components 145, which can include one or more edge portions of the implantable device. A suture-engagement component 145 can be (for example) part of or attached to (e.g., via welding) a can housing. For example, a suture-engagement component 145 can be welded to or monolithic with the can housing. In one instance, suture-engagement component 145 can include a metal (e.g., titanium) tab that extends out of a curved portion of can housing. Each suture-engagement component 145 can include one or more holes, such as a one or more suture-engagement holes 150 and one or more other holes 155. Each suture-engagement hole 150 may be sized to be large enough to allow a suture to be threaded through it (e.g., having a diameter that is at least 2, 5 or 10 times that of a suture) but size constrained (e.g., having a diameter that is less than 30, 20 or 10 times that of a suture) so as to constrain movement of the suture after the implantable device is implanted and sutured to an anatomical site. Each of the one or more other holes 155 may (for example) be larger in diameter than the suture-engagement holes 150. During an implantation process, a surgical tool may engage (e.g., may hook, grasp, etc.) the other hole to facilitate pulling or pushing the implantable device to a target location or target position.

FIG. 1B shows internal components 100b of the implantable pulse generator. Internal components 100b may be positioned within a can housing. Internal components 100b can include a rechargeable battery 160 and circuitry 165. Circuitry 165 can include (for example) over 100,000, over 200,000, or over 500,000 transistors; over 500,000, over 750,000 over 1,000,000 connections; and/or a sleep current than is less 1 µA, less than 2 µA, or less than 1 µA. Circuitry 165 can include a modular design.

Circuitry 165 can include battery charging and communication circuitry, which can monitor and control currents and voltages supplied to the battery. The battery charging and communication circuitry can further monitor a charge of the battery. The battery charging and communication can further receive and effect emergency wireless commands (e.g., received initially at the antenna and routed to the battery charging and communication circuitry) to (for example) reset, stop or resume stimulation.

Circuitry 165 can include monitoring circuitry that measures impedance of one or more stimulating electrodes and that monitors the status of stimulation. For example, the impedance can be measured using sub-threshold pulses (e.g., 10 µs, <100 µA). As another example, high-resolution stimulation waveforms can be detected and characterized to track the status of stimulation. Device-internal voltage or current measurements can also be accessed and characterized. The monitoring circuitry may (for example) locally evaluate one or more rules using the monitored data and/or may cause the monitored data to be transmitted to another device. For example, a rule may include a condition that is satisfied upon detecting that a stimulation waveform has a given property (e.g., an amplitude or frequency that exceeds a threshold) and/or that an impedance has a given property (e.g., exceeding a threshold that may be fixed or dependent on a stimulation parameter). When the condition is satisfied, the monitoring circuitry may cause a stimulation parameter to be changed and/or an alert signal to be transmitted.

Circuitry 165 can include stimulation (e.g., pulse-generating) circuitry. The stimulation circuitry can identify an amplitude, temporal pattern and/or current steering for stimulation. The stimulation circuitry can trigger and define (for example) low-frequency stimulation and high-frequency block (e.g., 1 Hz-50 kHz).

Internal components 100b can further include (for example) one or more sensors (e.g. an accelerometer), memory (e.g., a flash memory), a communication control (e.g., BLE matching circuitry), wireless power transfer (WPT) matching circuitry, one or more inductors (e.g., to generate high voltages for an integrated circuit including various circuitry), one or more micro-processing units (e.g., with Bluetooth capability) and/or a fusible resistor. For example, the memory may be used to store an event log and/or back-up firmware images.

Figure 2A:
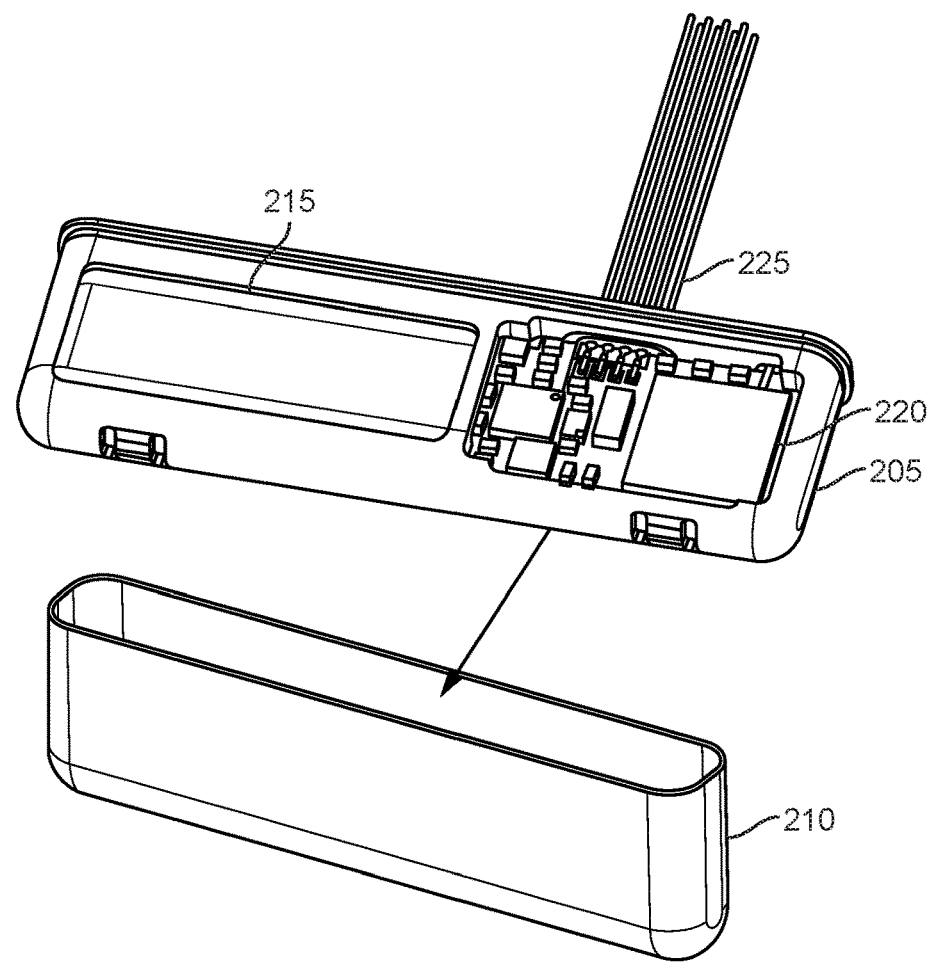
FIGS. 2A-2E show various stages during a process of manufacturing an implantable pulse generator according to an embodiment of the invention.
Figure 2B:
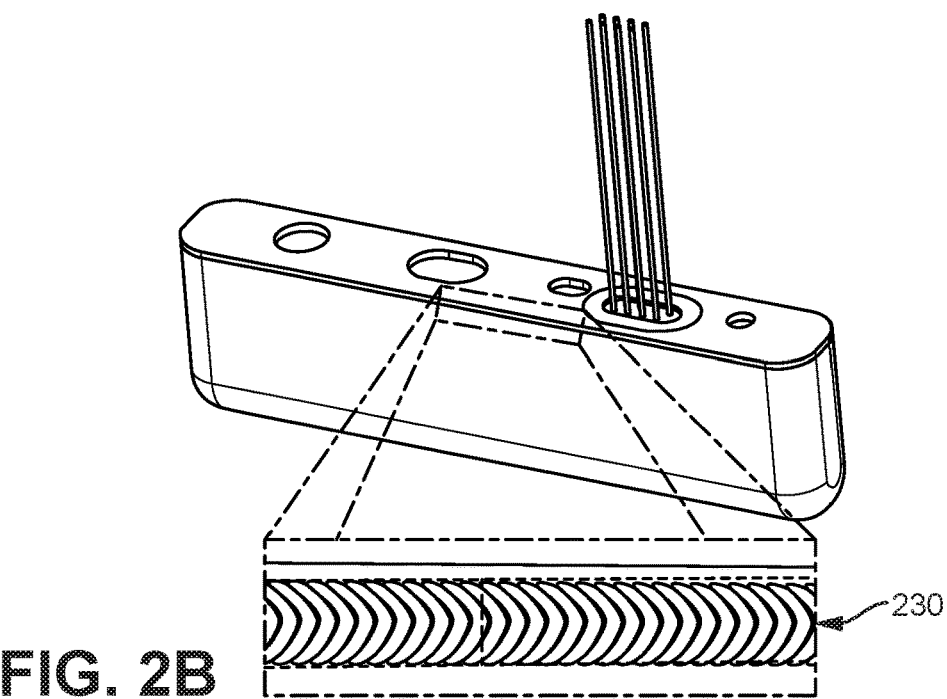

FIGS. 2A-2E show various stages during a process of manufacturing an implantable pulse generator according to an embodiment of the invention. In FIG. 2A, internal components 205 are positioned within a can housing 210. FIG. 2B shows internal components 205 positioned within can housing 210. Internal components 205 can include (for example) various components as disclosed herein (e.g., components described in relation to FIG. 1B). For example, internal components 205 can include a rechargeable battery 215 and a printed circuit board array 220 that includes various circuitry (e.g., pulse-generating circuitry). A set of connections 225 can connect to various circuitry in printed circuit board array 220 can extend out of a top surface of internal components 205 such that they are at least partly located outside of can housing 210 subsequent to positioning of internal components 205 within can housing 210.

Upon having positioned internal components 205 within can housing 210, a securing process can be performed to inhibit or prevent relative motion of internal components 205 and can housing 210. For example, a top perimeter of can housing 210 can be welded to a top perimeter of internal components, as illustrated in an exploded perimeter view 230 in FIG. 2B.

Figure 2C:
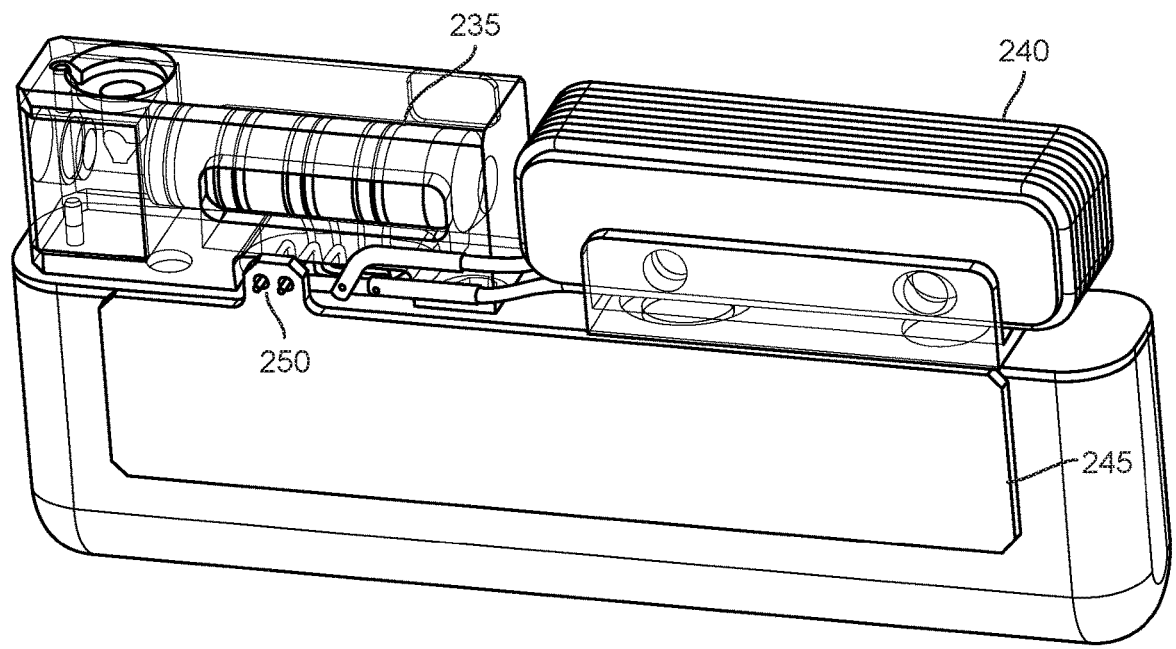

Header components can be positioned on a top surface of the housed internal components, as illustrated in FIG. 2C. The header components can include a coil 235 (e.g., to receive power from an external powering device and to avail the power via a connection to the battery) and one or more lead connections 240. One or more lead connections 240 can include a bond connector stack.

Further, an antenna 245 can be attached to (e.g., bonded to) on an outside of can housing 210. Contacts 250 of the antenna can be welded to one or more vias (e.g., to connect antenna 245 to circuitry and to a ground.

Each connection of set of connections 225 can be connected to a header component. For example, one or more of set of connections 225 can connect with lead connections 240, such that stimulation parameters (or stimulation voltage time series or triggers) can be communicated from circuitry housed in can housing 210 to lead connectors 240. As one (additional or alternative) example, a connection of set of connections can connect to coil 235, such that power from coil 235 can be availed to rechargeable battery 215. Connecting set of connections 225 to one or more header components can include (for example) welding an end of each connection to a contact corresponding to a header component.

Figure 2D:
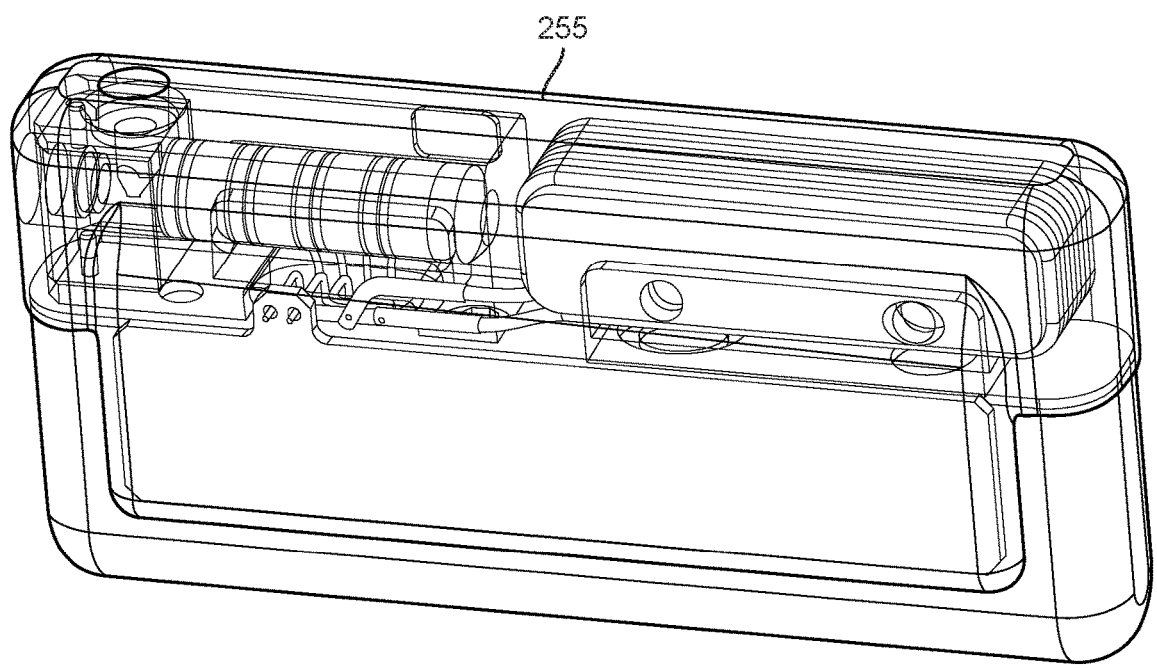

A header housing can be formed by applying (e.g., pouring) a header-housing material (e.g., a non-conductive material). For example, an epoxy material can be poured into a mold (e.g., that includes the header components positioned on the top surface of the housed internal components. The epoxy can then be cured to harden. FIG. 2D shows the header housing 265, which houses the header components. In some instances, the epoxy material covers the antenna. In some instances, a second pour of epoxy is used to cover the antenna in a separate process.

Figure 2E:
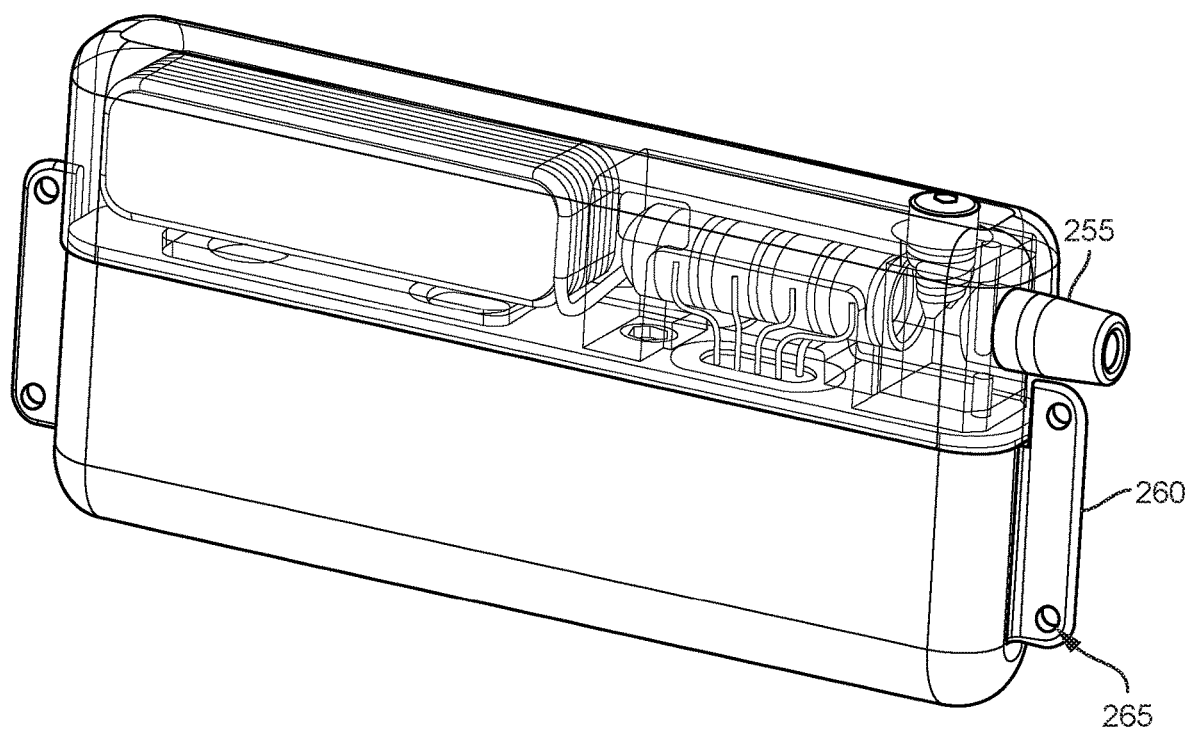

As shown in FIG. 2E, a silicone lead support 255 can be bonded to header housing 265. Silicone lead support 255 can be shaped to support and/or engage a lead, such that it can be connected to one or more lead connections 240 during an implantation process.

Further, a set of suture-engagement components 260 are attached to housing of the device. In this instance, an edge of each suture-engagement component 260 is laser welded to can housing 210. Each suture-engagement component 260 includes a set of holes 265 to receive a suture. It will be appreciated that alternative manufacture techniques are contemplated. For example, a can housing can be configured to include one or more holes 265. As another example, a suture-engagement component 260 can be bonded to the header housing instead of or in addition to securing suture-engagement component 260 to can housing 210.

Figure 3A:
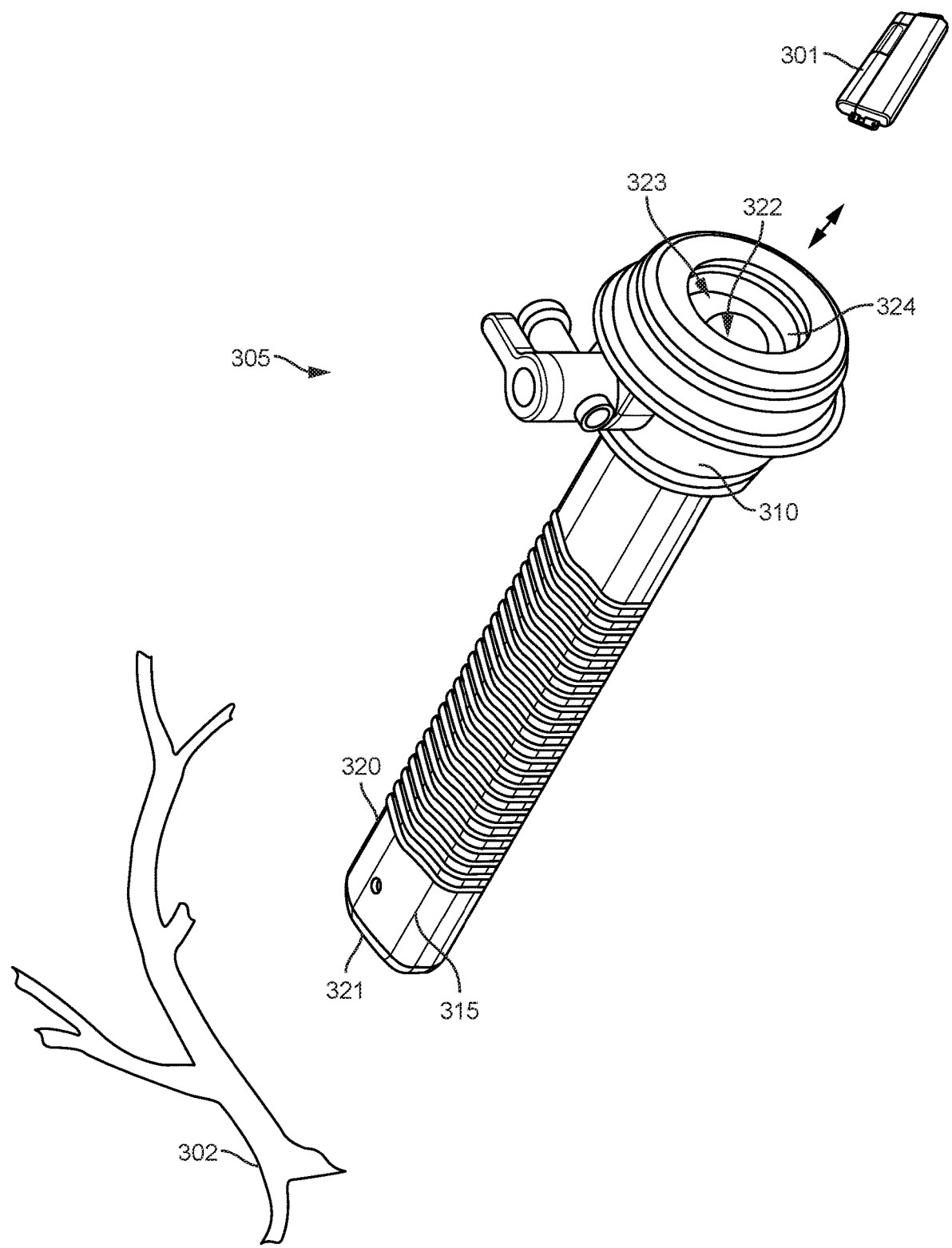
FIGS. 3A-3C illustrate various stages during a process of implanting an implantable pulse generator according to an embodiment of the invention.
Figure 3B:
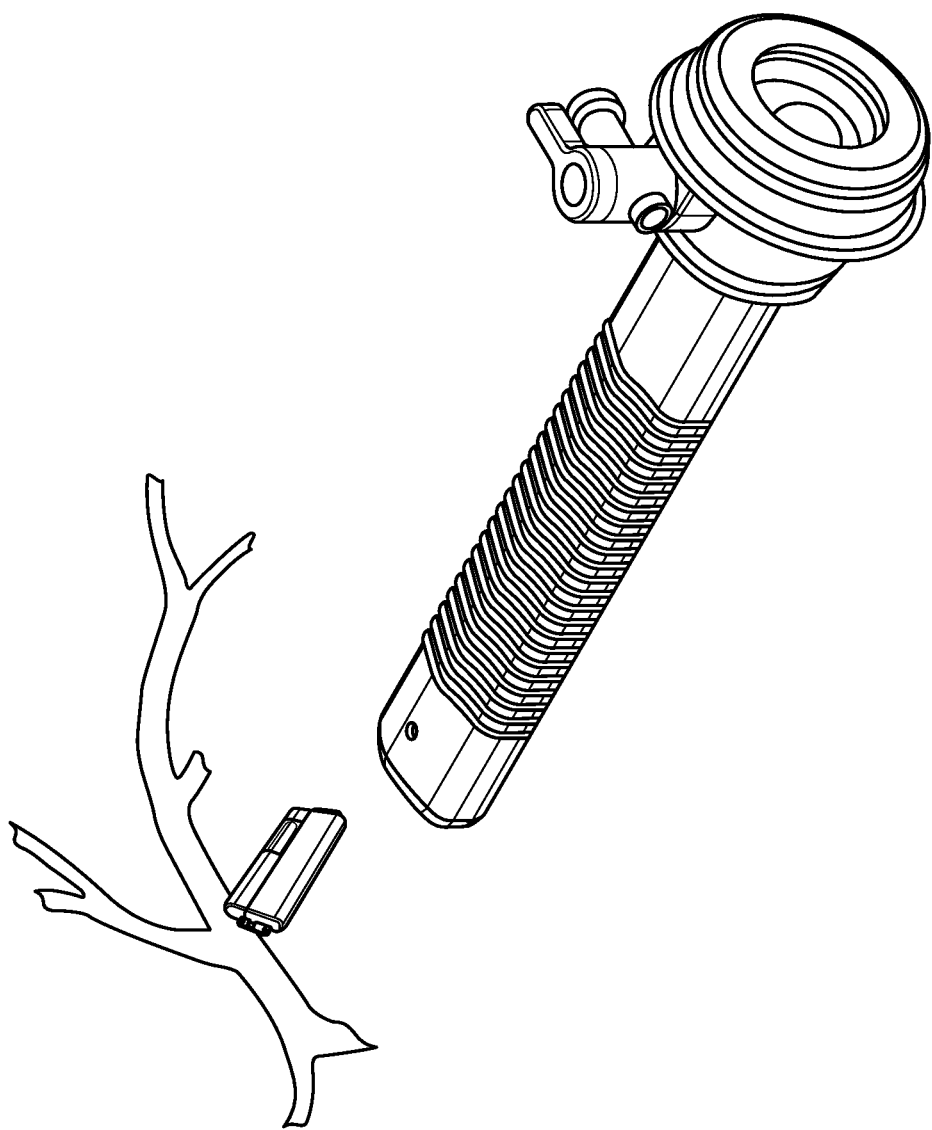
Figure 3C:
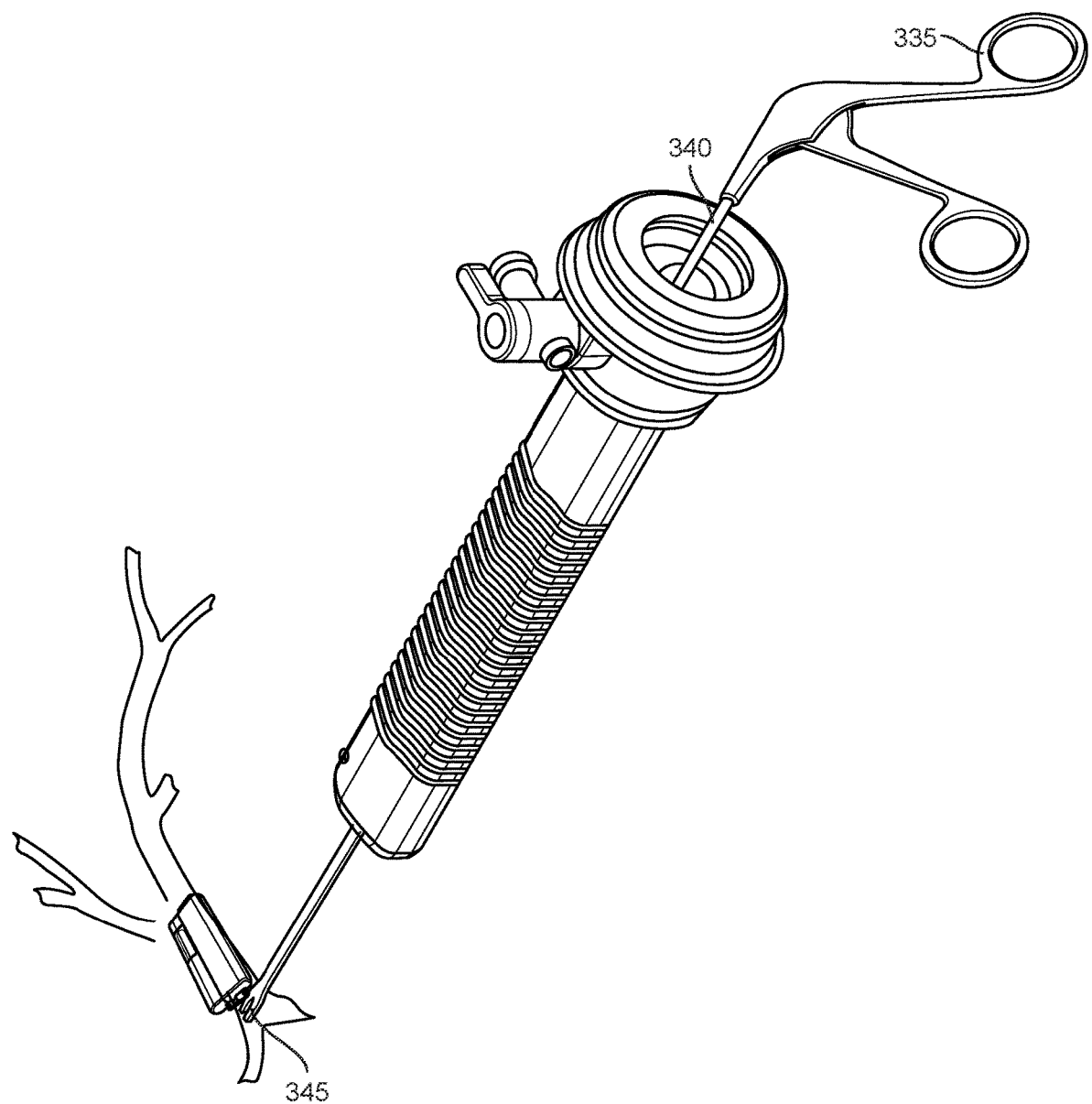

FIGS. 3A-3C illustrate various stages during a process of implanting an implantable pulse generator according to an embodiment of the invention. In some instances, an implantable device 301 can be moved to a target destination (e.g., near or at a target biological structure 302) by inserting implantable device 301 into a trocar 305. Trocar 305 can include a detachable obturator assembly (that includes an obturator housing, an obturator tip and an obturator body) (not pictured), a cannula assembly (that includes a cannula housing 310 and a cannula sleeve 315). The cannula assembly can include two or more openings to facilitate movement of various devices or parts of devices through cannula sleeve 315. Specifically, the cannula assembly can include a distal opening 321 of a sleeve body 320, a proximal opening 322 of sleeve body 320, a distal opening 323 of cannula housing 310, and a proximal opening 324 of cannula housing 310. Distal opening 321 of sleeve body 320 can be configured to attach (e.g., and detach) from the obturator body. The obturator assembly can be used to pierce through tissue to advance an edge of the trocar towards a target location.

A sequence of actions to be performed to position the trocar near a target location, as detailed in U.S. Provisional Application 62/669,485, filed on May 10, 2018, which is hereby incorporated by reference in its entirety for all purposes. For example, an incision can be made in a person's skin. The obturator assembly can be inserted through the incision. As the obturator assembly is advanced to a target location, the obturator tip dissects tissue to allow for movement of the trocar. The attached cannula assembly follows through the dissected portion. In some instances, when the obturator assembly reaches a location near a target location, the obturator assembly can be removed from cannula assembly, leaving the cannula assembly embedded through the tissue to function as a laparoscopic port to a target site.

One or more surgical instruments (e.g., one or more laparoscopic tools) can then be inserted into a proximal opening 322 of sleeve body 320 and extended through sleeve body 320, such that one or more ends of the surgical instrument(s) pass through a distal end 323 of cannula housing 310. The instruments may be used for manual dissection of biological structures to create a pathway to the target biological structure. For example, graspers can be inserted through one or more of cannula assemblies to move or dissect biological structures along natural tissue planes to provide a pathway to access the target biological structure. In other embodiments, graspers, dissectors, scissors, retractors, etc., are placed through the one or more of cannula assemblies for manipulations of the operative field or target biological structure by the user, e.g., a surgeon. Once the pathway is created, the one or more surgical instruments may be removed from the cannula assembly.

As shown in FIG. 3A, implantable device 301 can then be delivered through the cannula assembly into a target site of the target biological structure. In various embodiments, after the pathway is created to the target biological structure (and optionally a guidewire is inserted), implantable device 301 is fed through the cannula assembly into the target site. In some instances, implantable device 301 is introduced over a guidewire and guided through the cannula assembly and delivered into the target site. (FIG. 3B.) Additionally or alternatively, a lead assembly may be introduced over the guidewire and guided through the cannula assembly into the target site and delivered to the site of target biological structure 302. Implantable device 301 and a lead assembly may be delivered through the cannula assembly at the same time or separate from one another depending on the circumstances and type of neuromodulation system being used for therapy. For example (e.g., in an instance where the lead assembly is removable from implantable device 301), implantable device 301 may be delivered and implanted in the target site, and subsequently the lead assembly may be delivered, attached to target biological structure 302 and physically and electrically connected to implantable device 301.

As shown in FIG. 3C, a surgical instrument 330 can then be placed at least partly through the cannula assembly. Surgical instrument 330 can include one or more controls (e.g., handles 335), an extended portion 340 (e.g., having a width less than a width of sleeve body 320), and one or more distal controllable features 345. Surgical instrument 330 can be inserted into the cannula assembly such that one or more distal controllable features 345 fully traversed through sleeve body 320 and exited distal opening 321 of sleeve body 320, while the one or more controls remain outside of proximal opening 324 of cannula housing 310.

Surgical instrument 330 can be configured for manual manipulation of implantable device 301 and tissue within the target site to implant the implantable device 301 within the target site. For example, graspers can be inserted through one or more of cannula assemblies to move implantable device 301 and one or more sutures to attach implantable device to target biological structure 302. Surgical instrument 330 can include (for example) graspers. Distal controllable features 345 can be configured to open or close relative to each other in response to opening or closing of handles 335.

In some instances, one or more controls of surgical instrument 330 can be manipulated to cause one or more distal controllable features 345 to grasp a part (e.g., a suture-engagement component) of implantable device 301 to move and/or orient implantable device 301 in a desired location and/or desired position (e.g., corresponding to a location and/or position of target biological structure 302). One or more controls of surgical instrument 330 can further be used to cause one or more distal controllable features 345 to thread a suture through each of one, more or all holes (e.g., in each of one, more or all suture-engagement components) in implantable device 301 and through a part of target biological structure 302 and to knot the suture. For example, one or more distal controllable features 345 can grasp a needle attached to a suture and thread the needle through a hole in implantable device 301 and through a part of target biological structure 302. Surgical instrument 330 can be controlled so as to (for example) sequentially thread each of multiple sutures through an individual hole in implantable device 301 and a distinct position at target biological structure 302. In some instances, implantable device 301 can be secured to a target biological structure via at least or exactly two holes in implantable device 301 or via at least or exactly four holes in implantable device 301.

In some instances, one or more sutures and/or one or more needles are inserted to the target site through a cannula assembly of trocar 305. In some instances, one or more sutures and/or one or more needles are inserted to the target site through another cannula assembly of another trocar (e.g., the other cannula assembly being positioned such that a distal opening of the cannula assembly is within the target site and near the distal opening of the cannula assembly of trocar 305). In some instances, multiple surgical instruments are used to suture implantable device 301 to target biological structure 302 (e.g., each of which may be positioned through a different trocar). Upon having knotted a suture, the suture may be separated from a needle (e.g., by cutting the suture), and the needle may be subsequently removed from the target site (e.g., by grasping the needle using a surgical instrument and removing one or more distal controllable features 345 from trocar 305).

In instances in which implantable device 301 is not attached to a lead assembly prior to implantation and/or insertion through a trocar, a same or different surgical instrument can be used to connect one or more first ends of the lead assembly to implantable device 301 (e.g., after or before implantable device 301 is sutured to target biological structure). In some instances, a same or surgical instrument (e.g., and/or one or more same or different trocars) can be used to attach one or more second ends to one or more other target biological structures (or one or more other parts of target biological structure 302).

Upon having securely anchored each of implantable device 301 and the lead assembly, each cannula assembly and each surgical instrument (and optionally the guidewire) used in the process can be removed from the surgical site. Specifically, each surgical instrument (e.g., surgical instrument 330) and any guidewire can each be removed via a cannula assembly, and each trocar or cannula assembly can then be removed from the laparoscopic port(s). In some embodiments, the laparoscopic ports are closed using sutures, staples, or similar closing devices. Implantable device 301 remains implanted within the target site and the lead assembly remains attached to the target biological structure.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

It is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure.

While the principles of the disclosure have been described above in connection with specific apparatuses and methods, it is to be clearly understood that this description is made only by way of example and not as limitation on the scope of the disclosure.

What is claimed is:

1. An implantable pulse generator comprising:
   a power source;
   a wireless communication component configured to facilitate wireless communication with a non-implanted device;
   pulse-generating circuitry connected to the power source and configured to:
      identify, based on wireless communication with the non-implanted device, temporal and amplitude characteristics for electrical pulse stimuli; and
      trigger electrical output stimuli having the temporal and amplitude characteristics;
   one or more lead connections, wherein each lead connection of the one or more lead connections is:
      shaped to engage a lead; and
      electrically connected to the pulse-generating circuitry to enable the lead to deliver at least part of the electrical output stimuli triggered by the pulse-generating circuitry;
   one or more suture-engagement components, wherein each suture-engagement component of the one or more suture-engagement components includes one or more suture-engagement holes each having a diameter that is at least 0.1 mm and less than 5 mm, wherein the one or more suture-engagement components comprises titanium; and
   a surgical tool engagement hole for engaging with a surgical tool.

2. The implantable pulse generator of claim 1, wherein:
   a first suture-engagement component of the one or more suture-engagement components includes a first outer portion of the implantable pulse generator, wherein each of one or more first holes extend through, along a depth dimension, the first outer portion; and
   a second suture-engagement component of the one or more suture-engagement components includes a second outer portion of the implantable pulse generator, wherein one or more second holes extend through, along the depth dimension the second outer portion, wherein each of the one or more second holes is separated from at least one of the one or more first holes by a separation distance that is at least 90% of a length of the implantable pulse generator, wherein the length of the implantable pulse generator is perpendicular to and longer than each of a depth of the implantable pulse generator and a width of the implantable pulse generator.

3. The implantable pulse generator of claim 1, wherein the one or more suture-engagement components are configured such the one or more suture-engagement components include:
   at least one first hole, wherein each first hole of the at least one first hole:
      is positioned such that a center of the first hole is less than 5 mm from a first edge of the implantable pulse generator; and
      has a diameter that is at least 0.1 mm and less than 5 mm; and
   at least one second hole, wherein each second hole of the at least one second hole:
      is positioned such that a center of the second hole is less than 5 mm from a second edge of the implantable pulse generator, the second edge being opposite from and parallel to the first edge; and
      has a diameter that is at least 0.1 mm and less than 5 mm.

4. The implantable pulse generator of claim 1, further comprising:
   one or more housings, wherein each of the one or more housings at least partly encases:
      the power source;
      the wireless communication component; and/or
      the pulse-generating circuitry
   wherein each of the one or more suture-engagement components is attached to at least one of the one or more housings.

5. The implantable pulse generator of claim 1, wherein each of the one or more suture-engagement components includes a planar surface, and wherein each of the one or more suture-engagement holes extends through the planar surface.

6. The implantable pulse generator of claim 1, wherein each of the one or more suture-engagement components includes a wrapped surface, and wherein each of the one or more suture-engagement holes extends through two opposite portions of the wrapped surface.

7. The implantable pulse generator of claim 1, wherein each of the one or more suture-engagement components includes a metallic material.

8. The implantable pulse generator of claim 1, wherein the one or more suture-engagement components are configured so as to collectively include at least four holes.

9. The implantable pulse generator of claim 1, wherein each suture-engagement component of the one or more suture-engagement components includes one or more suture-engagement holes each having a diameter that is at least 0.5 mm and less than 2.5 mm.

10. The implantable pulse generator of claim 1, wherein the wireless communication component comprises an antenna that comprises one or more patterned planar conductive elements, wherein each of at least one of the one or more patterned planar conductive elements is positioned on an outer surface of the implantable pulse generator.

11. The implantable pulse generator of claim 1, further comprising:
   a can housing that houses the pulse-generating circuitry, wherein the wireless communication component comprises an antenna that is positioned such that at least part of the antenna is on a surface of the can housing.

12. The implantable pulse generator of claim 1, wherein the power source includes a rechargeable battery.

13. The implantable pulse generator of claim 1, wherein the one or more suture-engagement components are rigid.

14. A method for implanting an implantable pulse generator comprising:
- inserting a trocar into a person such that an obturator is near a target anatomical location, the trocar including the obturator and a cannula that extends from an opening in the trocar to the obturator;
- inserting an implantable pulse generator into the opening in the trocar to facilitate advancement of the implantable pulse generator through the cannula of the trocar, the implantable pulse generator including:
- pulse-generating circuitry configured to:
  - identify temporal and amplitude characteristics for electrical pulse stimuli; and
  - trigger electrical output stimuli having the temporal and amplitude characteristics;
- one or more lead connections, wherein each lead connection of the one or more lead connections is:
  - shaped to engage a lead; and
  - electrically connected to the pulse-generating circuitry to enable the lead to deliver at least part of the electrical output stimuli triggered by the pulse-generating circuitry;
- one or more rigid suture-engagement components, wherein each suture-engagement component of the one or more suture-engagement components includes one or more suture-engagement holes, wherein the one or more rigid suture-engagement components comprises titanium;
- positioning a suture grasper device such that a set of grasping jaws of the suture grasper device extend through the cannula of the trocar, tips of the set of grasping jaws are near the target anatomical location, and one or more handle controls remain outside of the opening, wherein the suture grasper device is configured such that one or more positions of the one or more handle controls control whether the tips of the set of grasping jaws are open or closed;
- controlling the one or more positions of the one or more handle controls across a period of time so as to cause the tips of the set of grasping jaws to facilitate:
- threading a suture through:
  - a hole of the one or more suture-engagement holes; and
  - an anatomical site at the target anatomical location;
- knotting the suture, to thereby at least partly affixed the implantable pulse generator to the target anatomical location.

15. The method for implanting the implantable pulse generator of claim 14, further comprising:
- inserting another trocar into the person such that another obturator of the other trocar is near the target anatomical location, the other trocar including the other obturator and another cannula that extends from another opening in the trocar to the other obturator;
- positioning another suture grasper device such that another set of grasping jaws of the other suture grasper device extend through the other cannula of the other trocar, other tips of the other set of grasping jaws are near the target anatomical location, and one or more other handle controls remain outside of the other opening, wherein the other suture grasper device is configured such that one or more other positions of the one or more other handle controls control whether the other tips of the other set of grasping jaws are open or closed;
- controlling the one or more other positions of the one or more other handle controls across a period of time so as to cause the tips of the other set of grasping jaws to further facilitate knotting the suture.

16. The method for implanting the implantable pulse generator of claim 14, wherein the one or more suture-engagement components includes a plurality of holes, and wherein the controlling the one or more positions of the one or more handle controls further cause the tips of the set of grasping jaws to facilitate, for each other hole of the plurality of holes;
- threading another suture through:
  - another hole of the plurality of holes; and
  - another anatomical site at the target anatomical location;
- knotting the other suture, to further affix the implantable pulse generator to the target anatomical location.

\* \* \* \* \*